US012692190B2

(12) United States Patent
Jiang et al.

(10) Patent No.: US 12,692,190 B2
(45) Date of Patent: Jul. 28, 2026

(54) METHOD FOR PREPARING ULTRA-THIN FLEXIBLE GLASS BY USING BIOMIMETIC WEATHERING ENZYME COMPOUND GLASS THINNING AGENT

(71) Applicant: BEIJING INSTITUTE OF FUTURE SCIENCE AND TECHNOLOGY ON BIOINSPIRED INTERFACE, Beijing (CN)

(72) Inventors: Lei Jiang, Beijing (CN); Dezhao Hao, Beijing (CN); Ye Tian, Beijing (CN)

(73) Assignee: BEIJING INSTITUTE OF FUTURE SCIENCE AND TECHNOLOGY ON BIOINSPIRED INTERFACE, Beijing (CN)

( * ) Notice: Subject to any disclaimer, the term of this patent is extended or adjusted under 35 U.S.C. 154(b) by 356 days.

(21) Appl. No.: 18/681,011

(22) PCT Filed: Feb. 16, 2023

(86) PCT No.: PCT/CN2023/076363
§ 371 (c)(1),
(2) Date: Feb. 2, 2024

(87) PCT Pub. No.: WO2023/207263
PCT Pub. Date: Nov. 2, 2023

(65) Prior Publication Data
US 2024/0270630 A1 Aug. 15, 2024

(30) Foreign Application Priority Data
Apr. 29, 2022 (CN) ......................... 202210466668.X

(51) Int. Cl.
*C03C 15/00* (2006.01)
*C12N 9/00* (2006.01)

(52) U.S. Cl.
CPC ................ *C03C 15/00* (2013.01); *C12N 9/00* (2013.01)

(58) Field of Classification Search
None
See application file for complete search history.

(56) References Cited

U.S. PATENT DOCUMENTS

| | | | |
|---|---|---|---|
| 3,839,113 A | 10/1974 | Yoshida et al. | |
| 2003/0056714 A1* | 3/2003 | Itl | C03C 4/0007 117/5 |
| 2012/0263945 A1* | 10/2012 | Yoshikawa | B32B 27/38 216/36 |

OTHER PUBLICATIONS

International Search Report issued in International Application No. PCT/CN2023/076363 mailed on Jun. 6, 2023 (5 pages).
(Continued)

*Primary Examiner* — Shamim Ahmed
(74) *Attorney, Agent, or Firm* — Osha Bergman Watanabe & Burton LLP

(57) ABSTRACT

A method for preparing ultra-thin flexible glass includes: extraction of biomimetic weathering enzyme, preparation of solution of biomimetic weathering enzyme glass thinning agent, and glass thinning. Extraction includes: dissolving a plant raw material of biomimetic weathering enzyme, adjusting pH, increasing stability of the solution, boiling and holding at a constant temperature, and filtering to obtain a first solution; adjusting pH of the first solution, precipitating and filtering to obtain a first precipitate; and then adjusting pH of the first precipitate, precipitating and filtering to obtain a second precipitate, and drying the second precipitate to obtain the biomimetic weathering enzyme in solid form. Preparation includes: adding 7-20 weight parts of water, 0.1-2 weight parts of stabilizer, 0.1-1 weight parts of pH regulator C, and 0.1-1 weight parts of adjuvant to 1 weight part of biomimetic weathering enzyme, and stirring (Continued)

the mixture to obtain solution of biomimetic weathering enzyme glass thinning agent.

10 Claims, 2 Drawing Sheets

(56) References Cited

OTHER PUBLICATIONS

Written Opinion issued in International Application No. PCT/CN2023/076363 mailed on Jun. 6, 2023 (5 pages).
Li Wei, "Functions of Typical Organisms and Carbonic Anhydrase thereof in Karst Ecosystem" Vo. 2005, No. 2. Feb. 15, 2005, pp. 1-142 text, p. 46, paragraph 1, and p. 58, paragraphs 1 and 3 (142 pages).

* cited by examiner

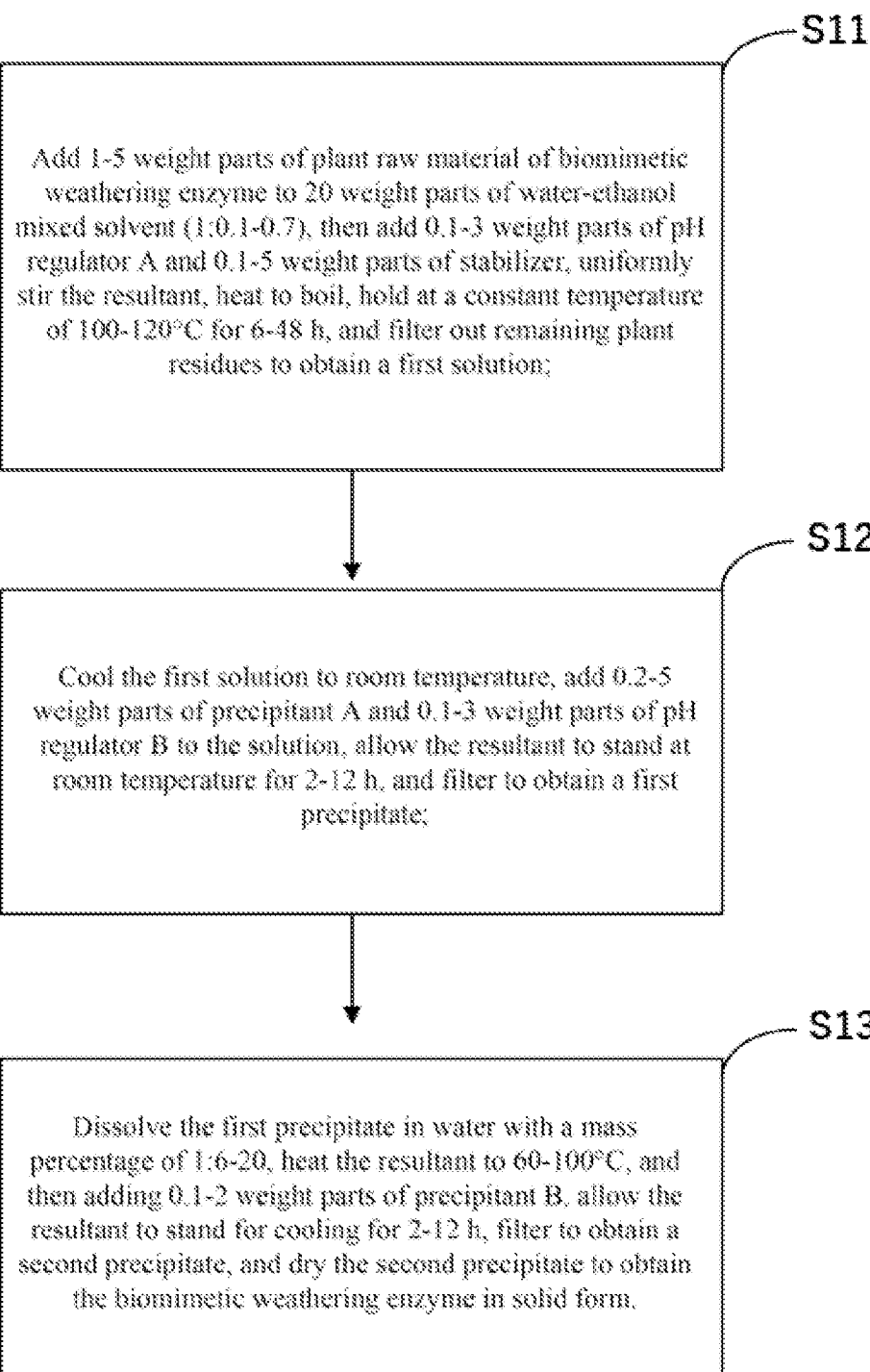

Add 1-5 weight parts of plant raw material of biomimetic weathering enzyme to 20 weight parts of water-ethanol mixed solvent (1:0.1-0.7), then add 0.1-3 weight parts of pH regulator A and 0.1-5 weight parts of stabilizer, uniformly stir the resultant, heat to boil, hold at a constant temperature of 100-120°C for 6-48 h, and filter out remaining plant residues to obtain a first solution;

S11

Cool the first solution to room temperature, add 0.2-5 weight parts of precipitant A and 0.1-3 weight parts of pH regulator B to the solution, allow the resultant to stand at room temperature for 2-12 h, and filter to obtain a first precipitate;

S12

Dissolve the first precipitate in water with a mass percentage of 1:6-20, heat the resultant to 60-100°C, and then adding 0.1-2 weight parts of precipitant B, allow the resultant to stand for cooling for 2-12 h, filter to obtain a second precipitate, and dry the second precipitate to obtain the biomimetic weathering enzyme in solid form.

METHOD FOR PREPARING ULTRA-THIN FLEXIBLE GLASS BY USING BIOMIMETIC WEATHERING ENZYME COMPOUND GLASS THINNING AGENT

FIELD OF THE INVENTION

The present invention relates to the technical field of glass, in particular to a method for preparing ultra-thin flexible glass by using biomimetic weathering enzyme compound glass thinning agent.

BACKGROUND OF THE INVENTION

Since the glass has good light transparency, scratch resistance and corrosion resistance performances, a current ultra-thin glass is predominantly used as an outermost protection layer of electronic display devices. However, the existing melt stretching methods and fluoride etching methods cannot produce sufficiently-thin and transparent glass with high yield, which cannot meet the demands for flexible screens. Therefore, the current flexible screens mainly use transparent polyimide thin film with much lower hardness than glass but extremely expensive as the protective layer.

An ultra-thin flexible glass film is usually prepared by using glass melt stretching and fluoride etching methods. Due to process reasons, the thickness of the ultra-thin glass prepared by the melt stretching method is usually above 200 microns, and fluorides need to be used for further chemical thinning. However, since fluoride is highly toxic and may easily lead to surface roughness of the glass during thinning, a complex cleaning process is required, and glass breakage and damage may occur during cleaning and subsequent tempering treatment.

The existing alkaline glass thinning agents are based on strong alkaline solutions to corrode silica, making it difficult for industrial applications, and their theoretical rate and flatness are poor.

SUMMARY OF THE INVENTION

The present invention is intended to solve the problems of high toxicity, strong corrosiveness, requirements of repeated etching/cleaning, and low yield in traditional fluoride-based glass thinning processes; and provides a method for preparing ultra-thin flexible glass by using biomimetic weathering enzyme compound glass thinning agent, by learning and imitating the principle that plants secrete biomimetic weathering enzyme to corrode rocks in nature, manually extracting and synthesizing biomimetic weathering enzyme, and dissolving glass by using the biomimetic weathering enzyme, and thus the glass is uniformly dissolved to obtain a relatively thinner ultra-thin flexible glass.

The present invention provides a method for preparing ultra-thin flexible glass by using biomimetic weathering enzyme compound glass thinning agent, comprising the following steps:

S1. Extraction of biomimetic weathering enzyme, comprising: dissolving a plant raw material of biomimetic weathering enzyme, adjusting pH, increasing stability of the solution, boiling the solution and holding at a constant temperature, and filtering to obtain a first solution; adjusting pH of the first solution, precipitating and filtering to obtain a first precipitate; and then adjusting pH of the first precipitate, precipitating and filtering to obtain a second precipitate, and drying the second precipitate to obtain a biomimetic weathering enzyme in solid form;

S2. Preparation of solution of biomimetic weathering enzyme glass thinning agent, comprising: adding 7-20 weight parts of water, 0.1-2 weight parts of stabilizer, 0.1-1 weight parts of pH regulator C, and 0.1-1 weight parts of adjuvant to 1 weight part of biomimetic weathering enzyme in solid form, and uniformly stirring the mixture to obtain the solution of biomimetic weathering enzyme glass thinning agent; and S3. Glass thinning, comprising: completely immersing a glass to be thinned in a container containing the solution of biomimetic weathering enzyme glass thinning agent, shaking at a constant temperature of 60-120° C. for 10-50 h, taking out and cleaning with water to obtain a thinned glass.

Preferably, the method for preparing ultra-thin flexible glass by using biomimetic weathering enzyme compound glass thinning agent described in the present invention further comprises step S4, S4. Repeated thinning, comprising: determining whether a thickness of the thinned glass has reached to a thinning target, if yes, the preparation of the ultra-thin flexible glass is completed; and if not, replacing the solution of biomimetic weathering enzyme glass thinning agent in the container of step S3 with an unused solution of biomimetic weathering enzyme glass thinning agent, and then repeating step S3.

Preferably, according to the method for preparing ultra-thin flexible glass by using biomimetic weathering enzyme compound glass thinning agent as described in the present invention, in step S3, the glass to be thinned is a silicate glass with a mass percentage of $SiO_2>65\%$, a mass percentage of $CaO<12\%$, a mass percentage of $MgO<8\%$, and a mass percentage of $Fe_2O_3<5\%$;

the silicate glass is any one selected from the group consisting of soda-lime glass, ultra-white glass, quartz glass, high borosilicate glass, and high aluminosilicate glass; and a work temperature of the solution of biomimetic weathering enzyme glass thinning agent is in a range of 25-120° C.

Preferably, according to the method for preparing ultra-thin flexible glass by using biomimetic weathering enzyme compound glass thinning agent as described in the present invention, in step S1, the plant raw material of biomimetic weathering enzyme is any one or more selected from the group consisting of Persimmon calyx, Liquorice, Gallnut, Astragalus, Catechu, Ginseng fruit root, Pine branch, Rice root, lichen, Tea, *Salvia miltiorrhiza*, Ginkgo leaf, Lychee root, Kiwifruit root, *Multiflora* rose root, *papaya* root.

Preferably, according to the method for preparing ultra-thin flexible glass by using biomimetic weathering enzyme compound glass thinning agent as described in the present invention, in step S2, the pH regulator C is any one or more selected from the group consisting of sodium hydroxide, potassium hydroxide, calcium hydroxide, calcium oxide, ammonia water, ethanolamine, diethanolamine, triethanolamine, and triethylamine; and the ammonia water has a concentration of 20-30%.

Preferably, according to the method for preparing ultra-thin flexible glass by using biomimetic weathering enzyme compound glass thinning agent as described in the present invention, the adjuvant in step S2 is any one or more selected from the group consisting of citric acid, citrate, ethylenediaminetetraacetic acid, ethylenediaminetetraacetate, tartaric acid, tartrate, potassium ferrocyanide, potassium sodium ferrocyanide, sodium sulfide, potassium sulfide, phosphoric acid, phosphate, tripolyphosphoric acid, tripolyphosphate, hexametaphosphoric acid and hexametaphosphate.

Preferably, according to the method for preparing ultra-thin flexible glass by using biomimetic weathering enzyme compound glass thinning agent as described in the present invention, the step S1 comprises the following steps:

S11. Dissolution, comprising: adding 1-5 weight parts of plant raw material of biomimetic weathering enzyme to 20 weight parts of water-ethanol mixed solvent, then adding 0.1-3 weight parts of pH regulator A and 0.1-5 weight parts of stabilizer, uniformly stirring the mixture and heating to boil, holding at a constant temperature of 100-120° C. for 6-48 h, and filtering out plant residues, to obtain the first solution;

S12. First filtration, comprising: cooling the first solution to room temperature, adding 0.2-5 weight parts of precipitant A and 0.1-3 weight parts of pH regulator B, standing at room temperature for 2-12 h, and then filtering to obtain the first precipitate; and S13. Second filtration, comprising: dissolving 1 weight part of the first precipitate with 6-20 weight parts of water, heating the mixture to 60-100° C., adding 0.1-2 weight parts of precipitant B, standing and cooling for 2-12 h, filtering to obtain the second precipitate, and drying the second precipitate to obtain the biomimetic weathering enzyme in solid form.

Preferably, according to the method for preparing ultra-thin flexible glass by using biomimetic weathering enzyme compound glass thinning agent as described in the present invention, the stabilizer in steps S11 and S2 is any one or more selected from the group consisting of benzoic acid, benzoate, sorbic acid, sorbate, diacetic acid, diacetate, dithionous acid, dithionite, p-dihydroxybenzene, tert-butyl p-dihydroxybenzene, o-dihydroxybenzene, tert-butyl o-dihydroxybenzene, pyrogallol, gallic acid, gallate, gallate ester, ascorbic acid, ascorbate, ascorbate ester, isoascorbic acid, ascorbate, and ascorbate ester.

Preferably, according to the method for preparing ultra-thin flexible glass by using biomimetic weathering enzyme compound glass thinning agent as described in the present invention, in step S11, the water-ethanol mixed solvent is a solution with a mass percentage of 1:0.1-0.7;

in step S11, the pH regulator A is any one or more selected from the group consisting of sodium bicarbonate, potassium bicarbonate, sodium carbonate, potassium carbonate, ammonia water, lime, ethanolamine, citric acid, citrate, tartaric acid and tartrate;

the ammonia water has a concentration of 20-30%; and in step S12, the pH regulator B is any one or more selected from the group consisting of magnesium oxide, magnesium hydroxide, calcium hydroxide, calcium oxide, acetic acid, acetate, citric acid, citrate, phosphoric acid, phosphate and borax.

Preferably, according to the method for preparing ultra-thin flexible glass by using biomimetic weathering enzyme compound glass thinning agent as described in the present invention, in step S12, the precipitant A is any one or more selected from the group consisting of tartaric acid, tartrate, malic acid, malate, phthalic acid, phthalate, citric acid, citrate, phosphoric acid, phosphate, polyphosphoric acid, polyphosphate, lactic acid, lactate, gluconic acid, gluconate, oxalic acid and oxalate;

in step S13, the precipitant B is any one or more selected from the group consisting of ethanolamine, diethanolamine, triethanolamine, trimethylamine, triethylamine, ethylenediamine, isopropylamine, tetramethylammonium hydroxide, tetraethylammonium hydroxide, tetrapropylammonium hydroxide and tetrabutylammonium hydroxide; and each of the tetramethylammonium hydroxide, tetraethylammonium hydroxide, tetrapropylammonium hydroxide and tetrabutylammonium hydroxide may be an aqueous solution with a concentration of 40%.

The technical solution of the present invention is to uniformly dissolve a glass by using biomimetic weathering enzyme, and then take out and clean to obtain a thinned glass film when a certain thickness is left. During the thinning process, uniformly surface thinning of the glass can be ensured, the obtained ultra-thin flexible glass has a flat and smooth surface, and its flexibility can meet the requirements of a flexible display screen.

An ultra-thin flexible glass film is usually prepared by using glass melt stretching and fluoride etching methods. Due to process reasons, a thickness of the ultra-thin glass prepared by the melt stretching method is usually above 200 microns, and fluorides need to be used for further chemical thinning. However, since fluoride is highly toxic and may easily lead to surface roughness of glass during thinning, a complex cleaning process is required, and glass breakage and damage may occur during cleaning and subsequent tempering treatment. Instead, in the present invention, the biomimetic weathering enzyme glass thinning agent may be used to uniformly and continuously thin the glass, ultra-thin glasses with a series of thicknesses can be obtained only by controlling the thinning time, the subsequent cleaning is simple, and the yield is high. The obtained ultra-thin flexible glass with a thickness of 20 microns can achieve a minimum bending radius of only 0.35 mm, and has a surface roughness Ra of less than 10 nm, a visible light transmittance under the pure glass condition is higher than 90%, and the hardness thereof is the same as that of a raw glass.

In order to solve the problems of high toxicity, strong corrosion, requirements of repeated etching/cleaning, and low yield in traditional fluoride-based glass thinning processes, the present invention achieves glass thinning by using a biomimetic weathering enzyme compound glass thinning agent. Compared with traditional techniques, the technique of the present invention avoids the process of repeated etching/cleaning, allows for static soaking for thinning, and thus avoids intermediate mixing and shaking processes, and makes glass less prone to break, thereby greatly improving the yield of glass during the glass thinning process. At the same time, the biomimetic weathering enzyme used in the present invention has low toxicity, simple cleaning, and high yield for ultra-thin glass production, and may be used to thin the glass to a predetermined thickness in one time.

However, the existing alkaline glass thinning agents are based on strong alkaline solutions to corrode silica, making it difficult for industrial applications, the theoretical rate is less than 30% of that of the biomimetic weathering enzyme glass thinning agent, and the flatness is even worse.

The method for preparing ultra-thin flexible glass by using biomimetic weathering enzyme compound glass thinning agent comprises the following steps:

[1] Extraction of biomimetic weathering enzyme, comprising:

adding 1-5 weight parts of plant raw material of biomimetic weathering enzyme to 20 weight parts of water-ethanol mixed solvent (1:0.1-0.7), then adding 0.1-3 weight parts of pH regulator A and 0.1-5 weight parts of stabilizer, boiling the solution, holding at a constant temperature of 100-120° C. for 6-48 h, and filtering out remaining plant residues;

cooling the resultant solution to room temperature, adding 0.2-5 weight parts of precipitant A and 0.1-3 weight parts of pH regulator B to the solution, allowing the resultant to stand at room temperature for 2-12 h, and filtering; and dissolving the filtered solid in water with a mass percentage of 1:6-20, heating the solution to 60-100° C., and then adding 0.1-2 weight parts of precipitant B, allowing the resultant to stand for cooling for 2-12 h, filtering, and drying to obtain the biomimetic weathering enzyme in solid form.

[2] Preparation of solution of biomimetic weathering enzyme glass thinning agent, comprising:

adding 7-20 weight parts of water, 0.1-2 weight parts of stabilizer, 0.1-1 weight part of pH regulator C, and 0.1-1 weight part of adjuvant to 1 weight part of biomimetic weathering enzyme in solid form to obtain the solution of biomimetic weathering enzyme glass thinning agent.

[3] Glass thinning process, comprising:

completely immersing a glass to be thinned in the solution of biomimetic weathering enzyme glass thinning agent, shaking at constant temperature of 60-120° C. for 10-50 h (according to the thickness reduction amount of the glass), and taking out and cleaning the thinned glass with water after the glass is thinned to a certain thickness.

For relatively thicker glass raw materials, multiple thinning is required. After the glass is thinned to a certain thickness in a first step, it is removed and put in a fresh solution of glass thinning agent to continue thinning.

The plant raw material of biomimetic weathering enzyme comprises one or more selected from the group consisting of Persimmon calyx, Liquorice, Gallnut, Astragalus, Catechu, Ginseng fruit root, Pine branch, Rice root, lichen, Tea, *Salvia miltiorrhiza*, Ginkgo leaf, Lychee root, Kiwifruit root, *Multiflora* rose root, *papaya* root.

A biomimetic weathering enzyme compound glass thinning agent consists of pH regulator C, biomimetic weathering enzyme, stabilizer, adjuvant, and water.

A work temperature of the biomimetic weathering enzyme compound glass thinning agent is between room temperature and boiling point of the solution (25-120° C.).

Types of glass that can be thinned comprise silicate glass with silica as a main component, such as soda lime glass, ultra-white glass, quartz glass, high borosilicate glass, high aluminosilicate glass, etc. The glass has a content of $SiO_2 > 65\%$, $CaO < 12\%$, $MgO < 8\%$, and $Fe_2O_3 < 5\%$.

The PH regulator A includes one or a mixture of sodium/potassium bicarbonate, sodium/potassium carbonate, ammonia water, lime, ethanolamine, citric acid and its salts, tartaric acid and its salts.

The PH regulator B includes one or a mixture of magnesium oxide, magnesium hydroxide, calcium hydroxide, calcium oxide, acetic acid and its salts, citric acid and its salts, phosphoric acid and its salts, and borax.

The PH regulator C includes one or a mixture of sodium hydroxide, potassium hydroxide, calcium hydroxide, calcium oxide, ammonia water, ethanolamine, diethanolamine, triethanolamine, trimethylamine and triethylamine.

The stabilizer includes one or a mixture of benzoic acid and its salts, sorbic acid and its salts, diacetic acid and its salts, dithionous acid and its salts, p-dihydroxybenzene, tert-butyl p-dihydroxybenzene, o-dihydroxybenzene, tert-butyl o-dihydroxybenzene, pyrogallol, gallic acid and its salts and esters, (iso) ascorbic acid and its salts and esters.

The precipitator A includes one or a mixture of tartaric acid and its salts, malic acid and its salts, phthalic acid and its salts, citric acid and its salts, phosphoric acid and its salts, polyphosphoric acid and its salts, lactic acid and its salts, gluconic acid and its salts, oxalic acid and its salts.

The precipitator B includes one or a mixture of ethanolamine, diethanolamine, triethanolamine, triethylamine, ethylenediamine, isopropylamine, tetramethylammonium hydroxide, tetraethylammonium hydroxide, tetrapropylammonium hydroxide and tetrabutylammonium hydroxide.

The adjuvant in the glass thinning agent includes one or a mixture of citric acid and its salts, ethylenediaminetetraacetic acid and its salts, tartaric acid and its salts, potassium/sodium ferrocyanide, sodium/potassium sulfide, phosphoric acid and its salts, tripolyphosphoric acid and its salts, hexametaphosphoric acid and its salts.

The present invention has the following advantages:

(1) In existing techniques, an ultra-thin flexible glass film is usually prepared by using glass melt stretching and fluoride etching methods, but due to process reasons, a thickness of the ultra-thin glass prepared by the melt stretching method is usually above 200 microns, and fluorides which are highly toxic and strongly corrosive need to be used for further chemical thinning. Instead, the biomimetic weathering enzyme compound glass thinning agent used in the present invention is based on the biomimetic weathering enzyme, which has low toxicity and is safer in use.

(2) In existing techniques, since fluoride thinning may easily lead to surface roughness of glass, a complex cleaning process is required, and glass breakage and damage may occur during cleaning and subsequent tempering treatment, and continuous thinning cannot be achieved either. Instead, in the present invention, the biomimetic weathering enzyme glass thinning agent may be used to uniformly and continuously dissolve the glass without causing surface roughness, such that the glass may be uniformly and continuously thinned. As long as a thinning time is controlled, ultra-thin glasses with a series of thicknesses may be obtained at high yield, with simple subsequent cleaning. The obtained ultra-thin flexible glass with a thickness of 20 microns can achieve a minimum bending radius of only 0.35 mm, and has a surface roughness Ra of less than 10 nm, a visible light transmittance under the pure glass condition is higher than 90%, and the hardness thereof is the same as that of a raw glass.

BRIEF DESCRIPTION OF THE DRAWINGS

FIG. 2 is a flowchart of step S1 of the method for preparing ultra-thin flexible glass by using biomimetic weathering enzyme compound glass thinning agent.

DETAILED DESCRIPTION OF THE EMBODIMENTS

Figure 1:
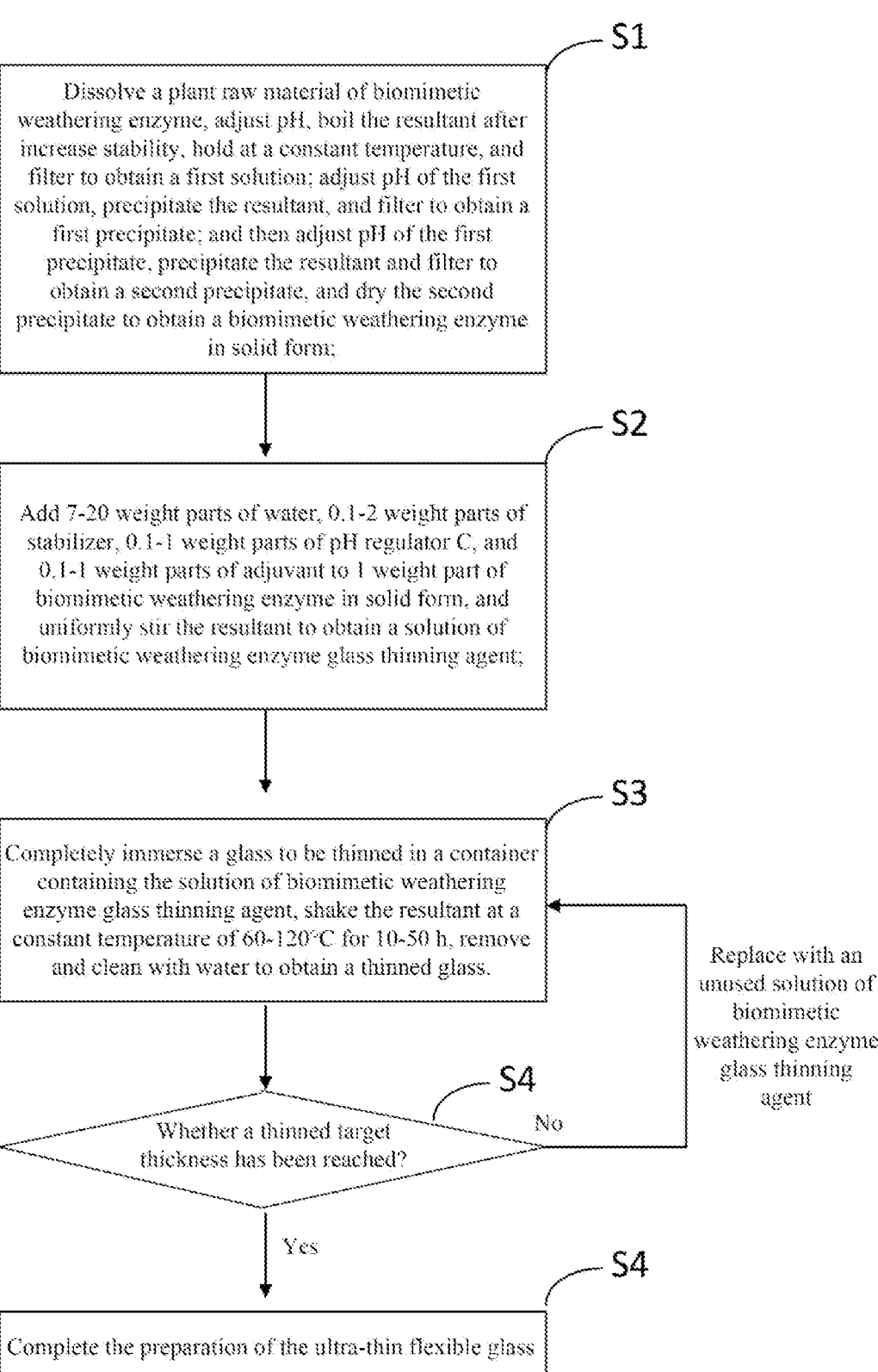
FIG. 1 is a flowchart of the method for preparing ultra-thin flexible glass by using biomimetic weathering enzyme compound glass thinning agent.

Hereafter, the technical solution of the present invention will be clearly and completely described based on the examples, in combination with the accompanying drawings. Obviously, the described examples are only a part of the examples of the present invention, but are not exhaustive.

Example 1

As shown in FIG. 1, a method for preparing ultra-thin flexible glass by using biomimetic weathering enzyme compound glass thinning agent comprises the following steps:

S1. Extraction of biomimetic weathering enzyme: a plant raw material of biomimetic weathering enzyme was dissolved, the pH was adjusted, the solution was boiled after increasing stability of the solution, held at a constant temperature, and filtered to obtain a first solution; the pH of the first solution was adjusted, the resultant was precipitated and filtered to obtain a first precipitate; and then the pH of the first precipitate was adjusted, the resultant was precipitated and filtered to obtain a second precipitate, and the second precipitate was dried to obtain the biomimetic weathering enzyme in solid form;

wherein, the plant raw material of biomimetic weathering enzyme is any one or more selected from the group consisting of Persimmon calyx, Liquorice, Gallnut, Astragalus, Catechu, Ginseng fruit root, Pine branch, Rice root, lichen, Tea, *Salvia miltiorrhiza*, Ginkgo leaf, Lychee root, Kiwifruit root, *Multiflora* rose root, *papaya* root.

As shown in FIG. 2, step S1 comprises the following steps:

S11. Dissolution: 1-5 weight parts of plant raw material of biomimetic weathering enzyme was added to 20 weight parts of water-ethanol mixed solvent, then 0.1-3 weight parts of pH regulator A and 0.1-5 weight parts of stabilizer were added, the resultant was uniformly stirred and heated to boil, held at a constant temperature of 100-120° C. for 6-48 h, and plant residues were filtered out, to obtain the first solution;

wherein, the stabilizer is any one or more selected from the group consisting of benzoic acid, benzoate, sorbic acid, sorbate, diacetic acid, diacetate, dithionous acid, dithionite, p-dihydroxybenzene, tert-butylp-dihydroxybenzene, o-dihydroxybenzene, tert-butylo-dihydroxybenzene, pyrogallol, gallic acid, gallate, gallate ester, ascorbic acid, ascorbate, ascorbate ester, isoascorbic acid, ascorbate, and ascorbate ester;

and the water-ethanol mixed solvent is a solution with a mass percentage of 1:0.1-0.7.

In step S11, the pH regulator A is any one or more selected from the group consisting of sodium bicarbonate, potassium bicarbonate, sodium carbonate, potassium carbonate, ammonia water, lime, ethanolamine, citric acid, citrate, tartaric acid and tartrate; and the ammonia water has a concentration of 20-30%.

S12. First filtration: the first solution was cooled to room temperature, 0.2-5 weight parts of precipitant A and 0.1-3 weight parts of pH regulator B were added, the resultant was allowed to stand at room temperature for 2-12 h, and then filtered to obtain the first precipitate;

wherein, the pH regulator B is any one or more selected from the group consisting of magnesium oxide, magnesium hydroxide, calcium hydroxide, calcium oxide, acetic acid, acetate, citric acid, citrate, phosphoric acid, phosphate and borax; and the precipitator A is any one or more selected from the group consisting of tartaric acid, tartrate, malic acid, malate, phthalic acid, phthalate, citric acid, citrate, phosphoric acid, phosphate, polyphosphoric acid, polyphosphate, lactic acid, lactate, gluconic acid, gluconate, oxalic acid and oxalate.

S13. Second filtration: 1 weight part of the first precipitate was dissolved with 6-20 weight parts of water, the resultant was heated to 60-100° C., then 0.1-2 weight parts of precipitate B was added, the resultant was allowed to stand for cooling for 2-12 h, filtered to obtain the second precipitate, and the second precipitate was dried to obtain the biomimetic weathering enzyme in solid form;

wherein, the precipitant B is any one or more selected from the group consisting of: ethanolamine, diethanolamine, triethanolamine, trimethylamine, triethylamine, ethylenediamine, isopropylamine, tetramethylammonium hydroxide, tetraethylammonium hydroxide, tetrapropylammonium hydroxide and tetrabutylammonium hydroxide; and each of the tetramethylammonium hydroxide, tetraethylammonium hydroxide, tetrapropylammonium hydroxide and tetrabutylammonium hydroxide may be an aqueous solution at a concentration of 40%.

S2. Preparation of solution of biomimetic weathering enzyme glass thinning agent: 7-20 weight parts of water, 0.1-2 weight parts of stabilizer, 0.1-1 weight parts of pH regulator C, and 0.1-1 weight parts of adjuvant were added to 1 weight part of biomimetic weathering enzyme in solid form, and the resultant was uniformly stirred to obtain the solution of biomimetic weathering enzyme glass thinning agent;

wherein, the pH regulator C is any one or more selected from the group consisting of: sodium hydroxide, potassium hydroxide, calcium hydroxide, calcium oxide, ammonia water, ethanolamine, diethanolamine, triethanolamine, and triethylamine;

the ammonia water has a concentration of 20-30%; and the adjuvant in step S2 is any one or more selected from the group consisting of citric acid, citrate, ethylenediaminetetraacetic acid, ethylenediaminetetraacetate, tartaric acid, tartrate, potassium ferrocyanide, potassium sodium ferrocyanide, sodium sulfide, potassium sulfide, phosphoric acid, phosphate, tripolyphosphoric acid, tripolyphosphate, hexametaphosphoric acid and hexametaphosphate.

S3. Glass thinning: a glass to be thinned was completely immersed in a container containing the solution of biomimetic weathering enzyme glass thinning agent, the resultant was shaken at a constant temperature of 60-120° C. for 10-50 h, removed and cleaned with water to obtain a thinned glass.

wherein, the glass to be thinned is a silicate glass with a mass percentage of $SiO_2 > 65\%$, a mass percentage of $CaO < 12\%$, a mass percentage of $MgO < 8\%$, and a mass percentage of $Fe_2O_3 < 5\%$;

the silicate glass is any one selected from the group consisting of soda-lime glass, ultra-white glass, quartz glass, high borosilicate glass, and high aluminosilicate glass; and the temperature at which the solution of biomimetic weathering enzyme glass thinning agent is used is 25-120° C.

S4. Repeated thinning: whether a thickness of the thinned glass has reached to a thinned target thickness was determined, if yes, the preparation of the ultra-thin flexible glass was completed; and if not, the solution of biomimetic weathering enzyme glass thinning agent in the container of step S3 was replaced with an unused solution of biomimetic weathering enzyme glass thinning agent, and then the step S3 was repeated.

Example 2

As shown in FIGS. 1-2, a method for preparing ultra-thin flexible glass by using biomimetic weathering enzyme compound glass thinning agent is proposed. The material to be thinned is an ultra-white glass, with an initial thickness of 180 μm and a size of 25*60 mm;

[1] Extraction of biomimetic weathering enzyme:

1.5 weight parts of Liquorice and 1 weight part of Rice root were ground to powder and added to 20 weight parts of water-ethanol mixed solvent (1:0.2), then 0.2 weight parts of potassium carbonate, 0.9 weight parts of ethanolamine and 0.1 weight parts of sodium isoascorbate were added, the resultant solution was boiled and held at a constant temperature of 100° C. for 26 h, and remaining plant residues were filtered out to obtain a first solution;

the first solution was cooled to room temperature, 0.8 weight parts of calcium gluconate and 0.5 weight parts of borax were added to the first solution, the resultant was allowed to stand at room temperature for 3 h, and filtered to obtain a first precipitate; and the first precipitate was dissolved in water with a mass percentage of 1:8, the resultant was heated to 85° C., and then 1 weight part of ethanolamine was added, the resultant was allowed to stand for cooling for 6 h, filtered to obtain a second precipitate, and the second precipitate was dried to obtain the biomimetic weathering enzyme in solid form.

[2] Preparation of solution of biomimetic weathering enzyme glass thinning agent:

9 weight parts of water, 0.7 weight parts of tert-butyl p-dihydroxybenzene, 0.15 weight parts of ammonia water (with a concentration of 25%), and 0.2 weight parts of trisodium citrate were added to 1 part of the biomimetic weathering enzyme in solid form to obtain the solution of biomimetic weathering enzyme glass thinning agent.

[3] Glass thinning process:

a glass to be thinned was completely immersed in the solution of biomimetic weathering enzyme glass thinning agent, the resultant was shaken at constant temperature of 95° C. for 14 h, and removed and cleaned to obtain a thinned glass. A shaker or mechanical device is used for shaking.

Properties of the thinned glass: a thickness of 25-27 μm, an in-plane thickness error<3 μm, a surface roughness Ra<5 nm, a visible light transmittance>90%, and a minimum bending radius<1.5 mm.

Example 3

As shown in FIGS. 1-2, a method for preparing ultra-thin flexible glass by using biomimetic weathering enzyme compound glass thinning agent is proposed. The material to be thinned is a high borosilicate glass, with an initial thickness of 200 μm and a size of 200*160 mm;

[1] Extraction of biomimetic weathering enzyme:

1.5 weight parts of Pine branch, 0.6 weight parts of Ginkgo leaf and 0.2 weight parts of Persimmon calyx were ground to power and added to 20 weight parts of water-ethanol mixed solvent (1:0.1), then 1.5 weight parts of sodium bicarbonate and 0.2 weight parts of sodium dithionite were added, the resultant solution was boiled and held at a constant temperature of 100° C. for 20 h, and remaining plant residues were filtered out;

the resultant solution was cooled to room temperature, 0.8 weight parts of sodium tripolyphosphate and 0.8 weight parts of magnesium hydroxide were added to the solution, the resultant was allowed to stand at room temperature for 2 h, and filtered; and the filtered solid was dissolved in water with a mass percentage of 1:16, the resultant was heated to 90° C., 0.5 weight parts of sodium hydroxide was added, the resultant was allowed to stand for cooling for 4 h, filtered, and dried to obtain the biomimetic weathering enzyme in solid form.

[2] Preparation of solution of biomimetic weathering enzyme glass thinning agent:

18 weight parts of water, 1.5 weight parts of gallic acid, 0.5 weight parts of sodium hydroxide, and 0.6 weight parts of tartaric acid were added to 1 part of the biomimetic weathering enzyme in solid form to obtain the solution of biomimetic weathering enzyme glass thinning agent.

[3] Glass thinning process:

a glass to be thinned was completely immersed in the solution of biomimetic weathering enzyme glass thinning agent, the resultant was shaken at constant temperature of 100° C. for 18 h, and removed and cleaned with water.

Properties of the thinned glass: a thickness of 18-20 μm, an in-plane thickness error<3 μm, a surface roughness Ra<5 nm, a visible light transmittance>90%, and a minimum bending radius<0.6 mm.

Example 4

As shown in FIGS. 1-2, a method for preparing ultra-thin flexible glass by using biomimetic weathering enzyme compound glass thinning agent is proposed. The material to be thinned is a quartz glass, with an initial thickness of 500 μm, and a size of 100*100 mm;

[1] Extraction of biomimetic weathering enzyme:

4 weight parts of *Salvia miltiorrhiza* was ground to powder and added to 20 weight parts of water-ethanol mixed solvent (1:0.6), then 2 weight parts of calcium hydroxide and 0.5 weight parts of potassium sorbate were added, the resultant solution was boiled and held at a constant temperature of 100° C. for 21 h, and remaining plant residues were filtered out;

the resultant solution was cooled to room temperature, 0.3 weight parts of potassium hydrogen phthalate, 1.2 weight parts of sodium acetate, and 0.2 weight parts of magnesium oxide were added to the solution, the resultant was allowed to stand at room temperature for 2 h, and filtered; and the filtered solid was dissolved in water with a mass percentage of 1:10, the resultant was heated to 95° C., 1.2 weight parts of triethanolamine was added, the resultant was allowed to stand for cooling for 3 h, filtered, and dried to obtain the biomimetic weathering enzyme in solid powder form.

[2] Preparation of solution of biomimetic weathering enzyme glass thinning agent:

13 weight parts of water, 1 weight part of sodium benzoate, 0.6 weight parts of triethylamine, and 0.3 weight parts of sodium sulfide were added to 1 part of biomimetic weathering enzyme in solid form to obtain the solution of biomimetic weathering enzyme glass thinning agent.

[3] Glass thinning process:

a glass to be thinned was completely immersed in the solution of biomimetic weathering enzyme glass thinning agent, the resultant was shaken at constant temperature of 90° C. for 24 h, and removed, the resultant was put in a new solution of biomimetic weathering enzyme glass thinning agent, and then shaken at a constant temperature of 90° C. for 24 h, and removed and cleaned with water.

Properties of the thinned glass: a thickness of 22-25 μm, an in-plane thickness error<3 μm, a surface roughness Ra<5 nm, a visible light transmittance>90%, and a minimum bending radius<1.8 mm.

The above description only illustrates preferred specific embodiments of the present invention, but the scope of protection of the present invention is not limited thereto. Within the technical scope disclosed by the present invention, equivalent replacements or modifications made by those skilled in the art based on the technical solution and inventive concept of the present invention should be covered within the scope of protection of the present invention.

The invention claimed is:

1. A method for preparing ultra-thin flexible glass by using biomimetic weathering enzyme compound glass thinning agent, comprising the following steps:

S1. Extraction of biomimetic weathering enzyme, comprising: dissolving a plant raw material of biomimetic weathering enzyme, adjusting pH, increasing stability of the solution, boiling the solution and holding at a constant temperature, and filtering to obtain a first solution; adjusting pH of the first solution, precipitating and filtering to obtain a first precipitate; and then adjusting pH of the first precipitate, precipitating and filtering to obtain a second precipitate, and drying the second precipitate to obtain the biomimetic weathering enzyme in solid form;

S2. Preparation of a solution of biomimetic weathering enzyme glass thinning agent, comprising: mixing 7-20 weight parts of water, 0.1-2 weight parts of stabilizer, 0.1-1 weight parts of pH regulator C, and 0.1-1 weight parts of adjuvant to 1 weight part of biomimetic weathering enzyme in solid form, to obtain the solution of biomimetic weathering enzyme glass thinning agent; and S3. Glass thinning, comprising: completely immersing a glass to be thinned in a container containing the solution of biomimetic weathering enzyme glass thinning agent, shaking at a constant temperature of 60-120° C. for 10-50 h, taking out and cleaning with water to obtain a thinned glass.

2. The method for preparing ultra-thin flexible glass by using biomimetic weathering enzyme compound glass thinning agent of claim 1, further comprising step S4, S4. Repeated thinning, comprising: determining whether a thickness of the thinned glass has reached to a thinning target, if yes, the preparation of the ultra-thin flexible glass is completed; and if not, replacing the solution of biomimetic weathering enzyme glass thinning agent in the container of step S3 with an unused solution of biomimetic weathering enzyme glass thinning agent, and then repeating step S3.

3. The method for preparing ultra-thin flexible glass by using biomimetic weathering enzyme compound glass thinning agent of claim 1, wherein, in step S3, the glass to be thinned is a silicate glass with a mass percentage of $SiO_2>65\%$, a mass percentage of $CaO<12\%$, a mass percentage of $MgO<8\%$, and a mass percentage of $Fe_2O_3<5\%$;

the silicate glass is any one selected from the group consisting of soda-lime glass, ultra-white glass, quartz glass, high borosilicate glass, and high aluminosilicate glass; and a work temperature of the solution of biomimetic weathering enzyme glass thinning agent is in a range of 25-120° C.

4. The method for preparing ultra-thin flexible glass by using biomimetic weathering enzyme compound glass thinning agent of claim 1, wherein, in step S1, the plant raw material of biomimetic weathering enzyme is any one or more selected from the group consisting of Persimmon calyx, Liquorice, Gallnut, *Astragalus, Catechu, Ginseng* fruit root, Pine branch, Rice root, lichen, Tea, *Salvia miltiorrhiza*, Ginkgo leaf, Lychee root, Kiwifruit root, *Multiflora* rose root, *papaya* root.

5. The method for preparing ultra-thin flexible glass by using biomimetic weathering enzyme compound glass thinning agent of claim 1, wherein, in step S2, the pH regulator C is any one or more selected from the group consisting of sodium hydroxide, potassium hydroxide, calcium hydroxide, calcium oxide, ammonia water, ethanolamine, diethanolamine, triethanolamine, and triethylamine; and the ammonia water has a concentration of 20-30%.

6. The method for preparing ultra-thin flexible glass by using biomimetic weathering enzyme compound glass thinning agent of claim 1, wherein, the adjuvant in step S2 is any one or more selected from the group consisting of citric acid, citrate, ethylenediaminetetraacetic acid, ethylenediaminetetraacetate, tartaric acid, tartrate, potassium ferrocyanide, potassium sodium ferrocyanide, sodium sulfide, potassium sulfide, phosphoric acid, phosphate, tripolyphosphoric acid, tripolyphosphate, hexametaphosphoric acid and hexametaphosphate.

7. The method for preparing ultra-thin flexible glass by using biomimetic weathering enzyme compound glass thinning agent of claim 1, wherein, the step S1 comprises the following steps:

S11. Dissolution, comprising: mixing 1-5 weight parts of plant raw material of biomimetic weathering enzyme to 20 weight parts of water-ethanol mixed solvent, then adding 0.1-3 weight parts of pH regulator A and 0.1-5 weight parts of stabilizer, and heating to boil, holding at a constant temperature of 100-120° C. for 6-48 h, and filtering out plant residues, to obtain the first solution;

S12. First filtration, comprising: cooling the first solution to room temperature, adding 0.2-5 weight parts of precipitant A and 0.1-3 weight parts of pH regulator B, standing at room temperature for 2-12 h, and then filtering to obtain the first precipitate; and S13. Second filtration, comprising: dissolving 1 weight part of the first precipitate with 6-20 weight parts of water, heating the solution to 60-100° C., adding 0.1-2 weight parts of precipitant B, standing and cooling for 2-12 h, filtering to obtain the second precipitate, and drying the second precipitate to obtain the biomimetic weathering enzyme in solid form.

8. The method for preparing ultra-thin flexible glass by using biomimetic weathering enzyme compound glass thinning agent of claim 7, wherein, in step S11, the water-ethanol mixed solvent is a solution with a mass percentage of 1:0.1-0.7;

in step S11, the pH regulator A is any one or more selected from the group consisting of sodium bicarbonate, potassium bicarbonate, sodium carbonate, potassium carbonate, ammonia water, lime, ethanolamine, citric acid, citrate, tartaric acid and tartrate;

the ammonia water has a concentration of 20-30%; and in step S12, the pH regulator B is any one or more selected from the group consisting of magnesium oxide, magnesium hydroxide, calcium hydroxide, calcium oxide, acetic acid, acetate, citric acid, citrate, phosphoric acid, phosphate and borax.

9. The method for preparing ultra-thin flexible glass using a biomimetic weathering enzyme compound glass thinning agent of claim 7, wherein, in step S12, the precipitant A is any one or more selected from the group consisting of: tartaric acid, tartrate, malic acid, malate, phthalic acid, phthalate, citric acid, citrate, phosphoric acid, phosphate, polyphosphoric acid, polyphosphate, lactic acid, lactate, gluconic acid, gluconate, oxalic acid and oxalate;

in step S13, the precipitant B is any one or more selected from the group consisting of: ethanolamine, diethanolamine, triethanolamine, trimethylamine, triethylamine, ethylenediamine, isopropylamine, tetramethylammonium hydroxide, tetraethylammonium hydroxide, tetrapropylammonium hydroxide and tetrabutylammonium hydroxide; and each of the tetramethylammonium hydroxide, tetraethylammonium hydroxide, tetrapropylammonium hydroxide and tetrabutylammonium hydroxide is an aqueous solutions at a concentration of 40%.

10. The method for preparing ultra-thin flexible glass using a biomimetic weathering enzyme compound glass thinning agent of claim 1, wherein, the stabilizer in steps S11 and S2 is any one or more selected from the group consisting of benzoic acid, benzoate, sorbic acid, sorbate, diacetic acid, diacetate, dithionous acid, dithionite, p-dihydroxybenzene, tert-butylp-dihydroxybenzene, o-dihydroxybenzene, tert-butylo-dihydroxybenzene, pyrogallol, gallic acid, gallate, gallate ester, ascorbic acid, ascorbate, ascorbate ester, isoascorbic acid, ascorbate, and ascorbate ester.

* * * * *